United States Patent
Friedman et al.

(10) Patent No.: US 9,932,583 B2
(45) Date of Patent: Apr. 3, 2018

(54) COMPOSITIONS AND METHODS FOR TREATING LIVER INJURY

(71) Applicant: The Children's Hospital of Philadelphia, Philadelphia, PA (US)

(72) Inventors: Joshua R. Friedman, Ardmore, PA (US); Nicholas J. Hand, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/119,036

(22) PCT Filed: Feb. 17, 2015

(86) PCT No.: PCT/US2015/016158
§ 371 (c)(1),
(2) Date: Aug. 15, 2016

(87) PCT Pub. No.: WO2015/123672
PCT Pub. Date: Aug. 20, 2015

(65) Prior Publication Data
US 2016/0355812 A1 Dec. 8, 2016

Related U.S. Application Data

(60) Provisional application No. 61/939,926, filed on Feb. 14, 2014.

(51) Int. Cl.
| | | |
|---|---|---|
| C12N 15/113 | (2010.01) | |
| C12Q 1/68 | (2018.01) | |
| A61K 31/713 | (2006.01) | |

(52) U.S. Cl.
CPC .......... *C12N 15/113* (2013.01); *C12Q 1/6883* (2013.01); *A61K 31/713* (2013.01); *C12N 2310/113* (2013.01); *C12N 2320/31* (2013.01); *C12Q 2600/178* (2013.01); *G01N 2800/085* (2013.01)

(58) Field of Classification Search
CPC ... A61K 48/00; C12N 15/113; C12N 2310/11
See application file for complete search history.

(56) References Cited

U.S. PATENT DOCUMENTS

| | | |
|---|---|---|
| 2012/0053229 A1 | 3/2012 | Naar |
| 2012/0238459 A1 | 9/2012 | Murakami |
| 2013/0323740 A1 | 12/2013 | Hoon et al. |

FOREIGN PATENT DOCUMENTS

| | | |
|---|---|---|
| WO | 2005/013901 | 2/2005 |
| WO | 2012/135848 | 10/2012 |

OTHER PUBLICATIONS

Gerhard et al., World J Hepatol, 2015, 7(2), 226-234.*
Ji, J., et al., "Over-expressed MicroRNA-27a and 27b Influence Fat Accumulation and Cell Proliferation During Rat Hepatic Stellate Cell Activation," FEBS Letters (2009) 583:759-766.
Rieger, J.K., et al., "Expression Variability of Absorption, Distribution, Metabolism, Excretion—Related MicroRNAs in Human Liver: Influence of Nongenetic Factors and Association with Gene Expression," Drug Metab. Dispos. (2013) 41:1752-1762.
Zahm, A.M., et al., "Rectal MicroRNAs are Perturbed in Pediatric Inflammatory Bowel Disease of the Colon," Journal of Crohn's and Colitis (2014) 8:1108-1117.
Hand, N.J., et al., "MicroRNA Profiling Identifies miR-29 as a Regulator of Disease-associated Pathways in Experimental Biliary Atresia," J. Pediatr. Gastroenterol. Nutr. (2012) 54(2):186-192.
Le Guen, C.L., et al., "Novel Targets of miR-30, a MicroRNA Required for Biliary Development," F1000Research (2013) 2:197.
Schug, J., et al., "Dynamic Recruitment of MicroRNAs to their mRNA Targets in the Regenerating Liver," BMC Genomics (2013) 14:264.
Wen, J., et al. "miR-122 Regulates Hepatic Lipid Metabolism and Tumor Suppression," : J. Clin. Invest. (2012) 122 (8):2773-2776.
Zahm, A.M., et al., "Circulating MicroRNA is a Biomarker of Biliary Atresia," J. Pediatr. Gastroenterol. Nutr. (2012) 55 (4):366-369.
Zahm, A.M., et al., "Circulating MicroRNA Is a Biomarker of Pediatric Crohn Disease," J. Pediatr. Gastroenterol. Nutr. (2011) 53(1):26-33.
Hand, N.J., et al. "The MicroRNA-30 Family is Required for Vertebrate Hepatobiliary Development," Gastroenterology (2009) 136(3):1081-1090.
Hand, N.J., et al., "Hepatic Function is Preserved in the Absence of Mature MicroRNAs" Hepatology (2009) 49:618-626.
Chu, A.S., et al., "A Role for MicroRNA in Cystic Liver and Kidney Diseases," : J. Clin. Invest. (2008) 118:3585-3587.
Wang, J., et al., "MicroRNA-182 downregulates metastasis suppressor 1 and contributes to metastasis of hepatocellular carcinoma" BMC Cancer (2012) 12:227.
Lu, M.H. et al., "microRNA-27b suppresses mouse MSC migration to the liver by targeting SDF-1α in vitro" Biochem Biophys. Res. Commun. (2012) 421(2):389-95.
Xu, C.F., et al., "Regulation of hepatic microRNA expression in response to ischemic preconditioning following ischemia/reperfusion injury in mice" OMICS (2009) 13(6):513-20.
Dolganiuc, A., et al., "MicroRNA expression profile in Lieber-DeCarli diet-induced alcoholic and methionine choline deficient diet-induced nonalcoholic steatohepatitis models in mice" Alcohol Clin. Exp. Res. (2009) 33(10):1704-10.
Chen, R.X., et al., "Suppression of microRNA-96 expression inhibits the invasion of hepatocellular carcinoma cells" Mol. Med. Rep. (2012) 5:800-804.
Wu, X.J., et al., "miR-27a as an Oncogenic microRNA of Hepatitis B Virus-related Hepatocellular Carcinoma" Asian Pacific J. Cancer Prev. (2013) 14(2):885-889.
Zhang, Q.H., et al., "Meta-analysis of microRNA-183 family expression in human cancer studies comparing cancer tissues with noncancerous tissues" Gene (2013) 527:26-32.

* cited by examiner

*Primary Examiner* — Amy H Bowman
(74) *Attorney, Agent, or Firm* — Robert C. Netter, Jr.; Dann, Dorfman, Herrell & Skillman

(57) ABSTRACT

Compositions and methods for detecting, inhibiting, treating, and/or preventing a liver disease or disorder such as cholestasis or fibrotic liver disease are provided.

20 Claims, 5 Drawing Sheets

```
                              SEQUENCE LISTING

<160> NUMBER OF SEQ ID NOS: 18

<210> SEQ ID NO 1
<211> LENGTH: 73
<212> TYPE: DNA
<213> ORGANISM: Homo sapiens

<400> SEQUENCE: 1
ggccggctgg ggttcctggg gatgggattt gcttcctgtc acaaatcaca ttgccaggga      60
tttccaaccg acc                                                        73

<210> SEQ ID NO 2
<211> LENGTH: 22
<212> TYPE: RNA
<213> ORGANISM: Homo sapiens

<400> SEQUENCE: 2
gggguuccug gggaugggau uu                                              22

<210> SEQ ID NO 3
<211> LENGTH: 21
<212> TYPE: RNA
<213> ORGANISM: Homo sapiens

<400> SEQUENCE: 3
aucacauugc cagggauuuc c                                               21

<210> SEQ ID NO 4
<211> LENGTH: 78
<212> TYPE: DNA
<213> ORGANISM: Homo sapiens

<400> SEQUENCE: 4
ctgaggagca gggcttagct gcttgtgagc agggtccaca ccaagtcgtg ttcacagtgg      60
ctaagttccg cccccccag                                                  78

<210> SEQ ID NO 5
<211> LENGTH: 22
<212> TYPE: RNA
<213> ORGANISM: Homo sapiens

<400> SEQUENCE: 5
agggcuuagc ugcuugugag ca                                              22
```

```
<210> SEQ ID NO 6
<211> LENGTH: 21
<212> TYPE: RNA
<213> ORGANISM: Homo sapiens

<400> SEQUENCE: 6
uucacagugg cuaaguuccg c                                           21

<210> SEQ ID NO 7
<211> LENGTH: 68
<212> TYPE: DNA
<213> ORGANISM: Homo sapiens

<400> SEQUENCE: 7
ctccggtgcc tactgagctg atatcagttc tcattttaca cactggctca gttcagcagg    60
aacaggag                                                             68

<210> SEQ ID NO 8
<211> LENGTH: 22
<212> TYPE: RNA
<213> ORGANISM: Homo sapiens

<400> SEQUENCE: 8
ugccuacuga gcugauauca gu                                          22

<210> SEQ ID NO 9
<211> LENGTH: 22
<212> TYPE: RNA
<213> ORGANISM: Homo sapiens

<400> SEQUENCE: 9
uggcucaguu cagcaggaac ag                                          22

<210> SEQ ID NO 10
<211> LENGTH: 110
<212> TYPE: DNA
<213> ORGANISM: Homo sapiens

<400> SEQUENCE: 10
ccgcagagtg tgactcctgt tctgtgtatg gcactggtag aattcactgt gaacagtctc    60
agtcagtgaa ttaccgaagg gccataaaca gagcagagac agatccacga              110

<210> SEQ ID NO 11
<211> LENGTH: 22
<212> TYPE: RNA
<213> ORGANISM: Homo sapiens

<400> SEQUENCE: 11
uauggcacug guagaauuca cu                                          22

<210> SEQ ID NO 12
<211> LENGTH: 22
<212> TYPE: RNA
<213> ORGANISM: Homo sapiens

<400> SEQUENCE: 12
gugaauuacc gaagggccau aa                                          22

<210> SEQ ID NO 13
<211> LENGTH: 78
<212> TYPE: DNA
<213> ORGANISM: Homo sapiens
```

```
<400> SEQUENCE: 13
tggccgattt tggcactagc acatttttgc ttgtgtctct ccgctctgag caatcatgtg     60
cagtgccaat atgggaaa                                                  78

<210> SEQ ID NO 14
<211> LENGTH: 23
<212> TYPE: RNA
<213> ORGANISM: Homo sapiens

<400> SEQUENCE: 14
uuuggcacua gcacauuuuu gcu                                            23

<210> SEQ ID NO 15
<211> LENGTH: 22
<212> TYPE: RNA
<213> ORGANISM: Homo sapiens

<400> SEQUENCE: 15
aaucaugugc agugccaaua ug                                             22

<210> SEQ ID NO 16
<211> LENGTH: 110
<212> TYPE: DNA
<213> ORGANISM: Homo sapiens

<400> SEQUENCE: 16
gagctgcttg cctcccccg tttttggcaa tggtagaact cacactggtg aggtaacagg      60
atccggtggt tctagacttg ccaactatgg ggcgaggact cagccggcac               110

<210> SEQ ID NO 17
<211> LENGTH: 24
<212> TYPE: RNA
<213> ORGANISM: Homo sapiens

<400> SEQUENCE: 17
uuuggcaaug guagaacuca cacu                                           24

<210> SEQ ID NO 18
<211> LENGTH: 21
<212> TYPE: RNA
<213> ORGANISM: Homo sapiens

<400> SEQUENCE: 18
ugguucuaga cuugccaacu a                                              21
```

COMPOSITIONS AND METHODS FOR TREATING LIVER INJURY

Figure 1:
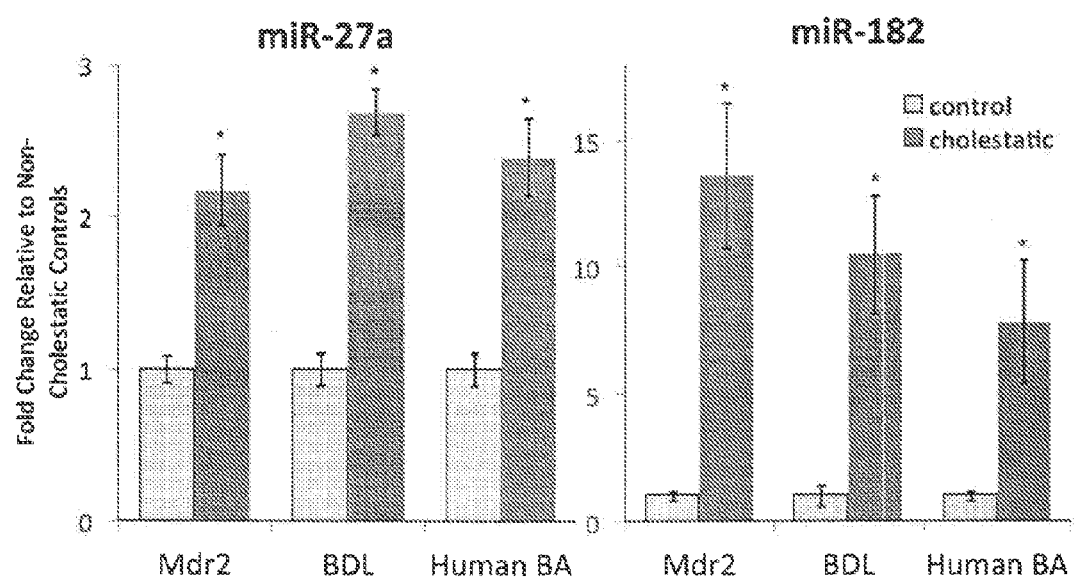

This application is a § 371 application of PCT/US2015/016158, filed Feb. 17, 2015, which claims priority under 35 U.S.C. § 119(e) to U.S. Provisional Patent Application No. 61/939,926, filed Feb. 14, 2014. The foregoing applications are incorporated by reference herein.

This invention was made with government support under Grant No. R01 DK079881 awarded by the National Institute of Diabetes and Digestive and Kidney Diseases (NIDDK). The Government has certain rights in this invention.

FIELD OF THE INVENTION

The present invention relates to the field of liver diseases and disorders, particularly cholestasis. Specifically, compositions and methods for treating, inhibiting, and/or preventing cholestasis are disclosed.

BACKGROUND OF THE INVENTION

Several publications and patent documents are cited throughout the specification in order to describe the state of the art to which this invention pertains. Each of these citations is incorporated herein by reference as though set forth in full.

Cholestasis is the state of impaired synthesis or excretion of bile, and it is the final common endpoint of a wide variety of infectious, inflammatory, genetic, toxic, and vascular diseases of the liver. The accumulation of bile components, particularly bile acids, is toxic to the liver, and chronic cholestasis leads to progressive fibrosis, cirrhosis, liver failure, and death if untreated (Kosters et al. (2008) Xenobiotica 38:1043-71). Cholestasis is caused by a variety of infectious, obstructive, metabolic and developmental liver disorders. Advances in the understanding of the hepatic response to cholestasis may therefore have an impact on a large population of adults and children with liver disease.

Cholestasis exposes hepatocytes and cholangiocytes to elevated levels of toxins normally excreted into the small intestine, including bile acids, heavy metals, and xenobiotics. Not surprisingly, the cycle of bile acid synthesis, canalicular excretion, intestinal absorption, and import into hepatocytes is regulated by feedback mechanisms (Wagner et al. (2010) Seminars Liver Dis., 30:160-77). Most of these are based on the ability of nuclear receptor transcription factors (NRs) to detect intracellular concentrations of bile acids and other bile components. In hepatocytes, NRs repress the expression of bile acid importers and synthetic enzymes, while activating export genes. NRs primarily involved in other metabolic pathways can also influence biliary function; for example, the lipid sensor PPARγ regulates CYP7A1, the rate-limiting enzyme in bile acid synthesis, as well as the phospholipid transporter MDR3 (Mdr2 in mouse) (Marrapodi et al. (2000) J. Lipid Res., 41:514-20; Kok et al. (2003) Biochem. J., 369:539-47). Nevertheless, these homeostatic pathways are not able to protect the liver in the setting of many cholestatic diseases. As a result, cholestatic damage progresses to biliary cirrhosis and liver failure. Progress in treating patients with cholestatic disease requires a greater understanding of the molecular pathways regulating bile flow and the cellular response to chronically elevated bile acids.

SUMMARY OF THE INVENTION

In accordance with the present invention, methods of inhibiting, treating, and/or preventing a disease or disorder associated with the liver (e.g., liver injury) are provided. In a particular embodiment, the disease or disorder associated with the liver is liver fibrosis. In a particular embodiment, the disease or disorder associated with the liver is cholestasis. In a particular embodiment, the method comprises administering to the subject at least one agent which inhibits the miR-27a cluster and/or the miR-182 cluster, particularly in the liver of the subject. In a particular embodiment, the method comprises administering at least one inhibitory nucleic acid molecule (e.g., siRNA, antisense, shRNA, etc., particularly an antisense oligonucleotide) which specifically hybridizes with the miR-27a cluster and/or the miR-182 cluster, particularly miR-27a and/or miR-182. The antisense oligonucleotide(s) may be administered in an expression vector, such as an AAV vector.

BRIEF DESCRIPTIONS OF THE DRAWING

FIG. 1 shows that miR-27a and miR-182 are induced by cholestasis. Hepatic miRNA was measured by quantitative PCR (qPCR) in 8 week old Mdr2$^{-/-}$ vs. wild-type (WT) mice, bile duct ligation mice (BDL) vs. sham treated mice (15 days post-ligation), and human clinical samples from children with biliary atresia or non-cholestatic disease control samples. n=4-6 for mouse; n=8 for human liver samples. $p<0.05$ for all pairs.

Figure 2:
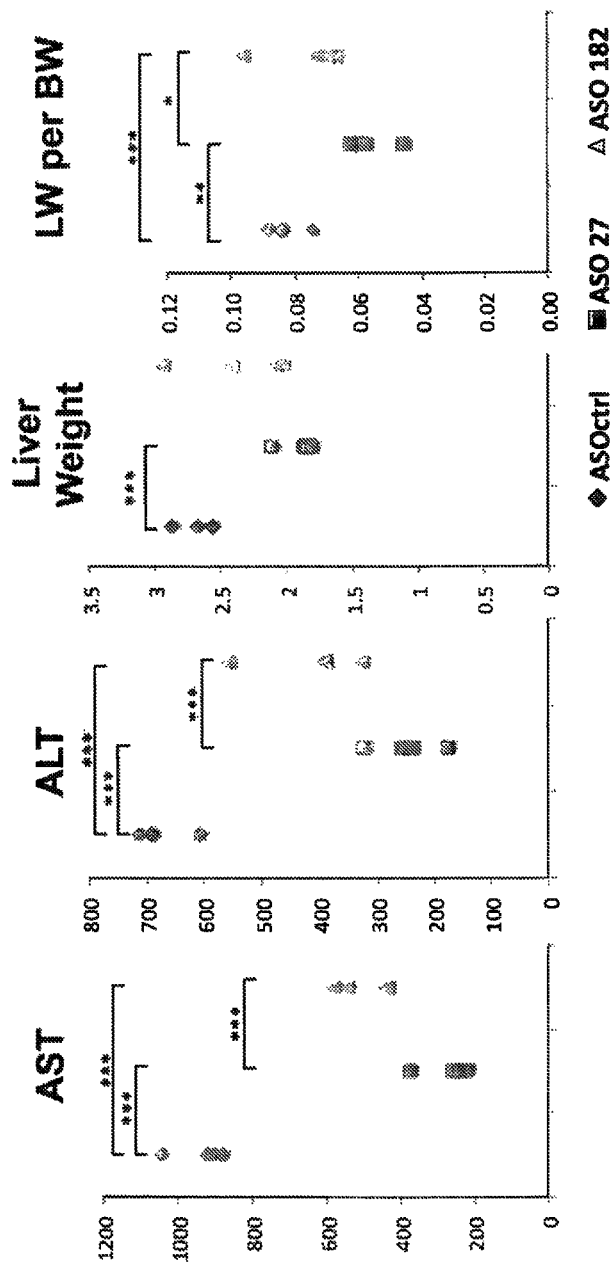

FIG. 2 shows the effects of antisense oligonucleotide (ASO) treatment on Mdr2 null male mice. Treatment with ASO27 and ASO182 significantly decreased transaminitis relative to control ASO. Treatment with ASO27 significantly reduced hepatomegaly. Significant differences are bracketed: *$p<0.05$; $p<0.01$; * $p<0.001$.

Figure 3A:
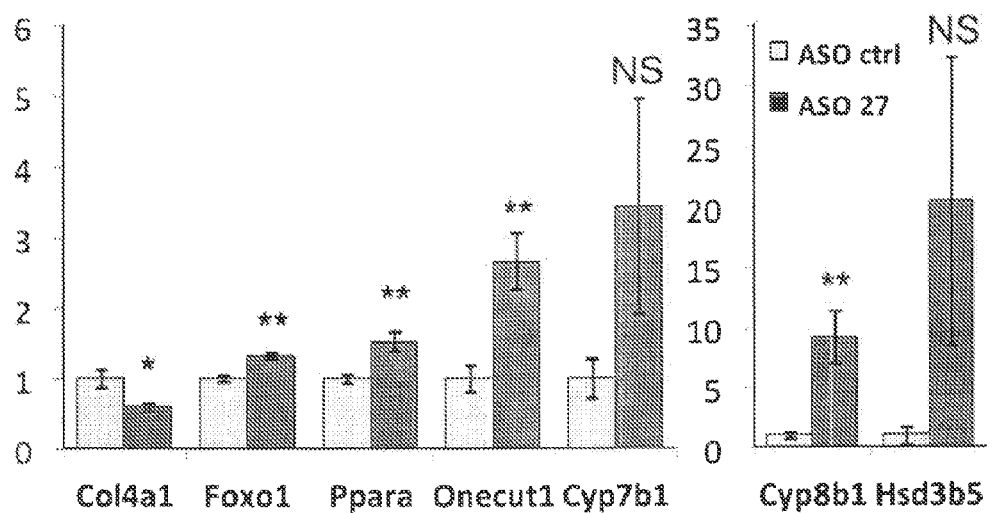
Figure 3B:
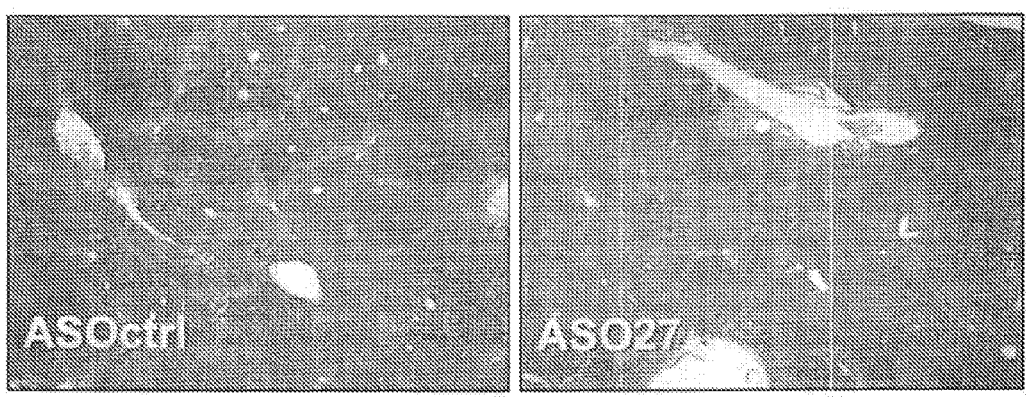
Figure 3C:
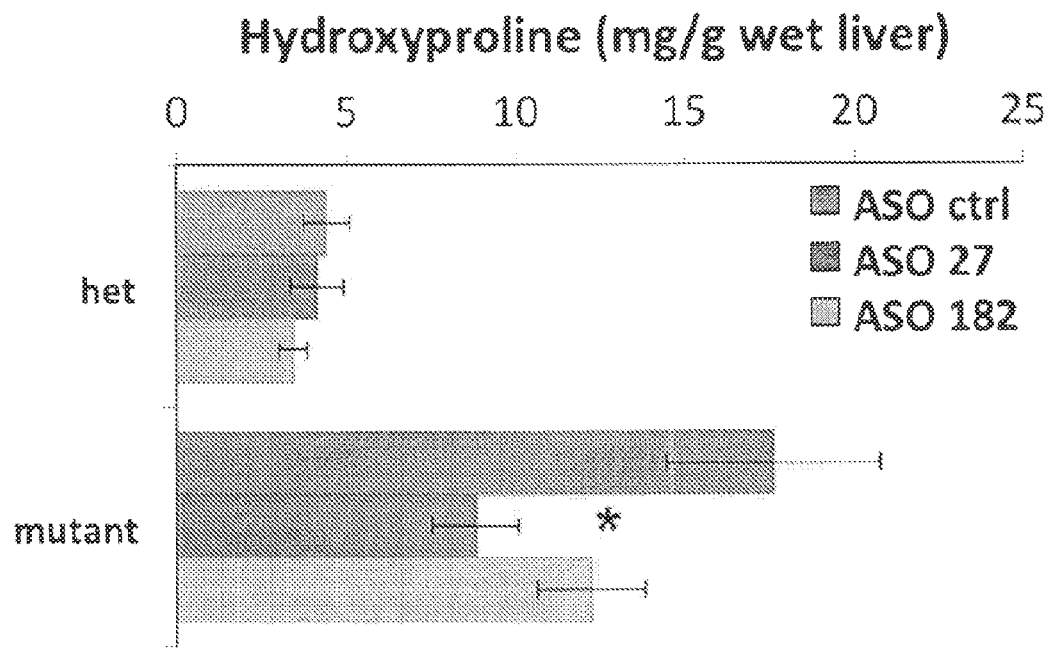
Figure 3D:
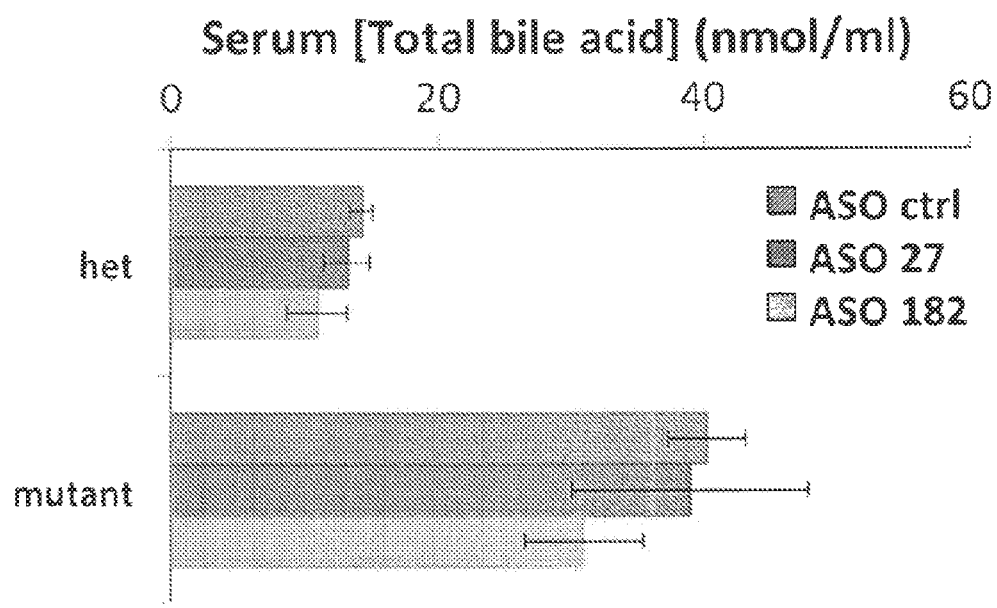

FIGS. 3A-3D show that ASO27 affects gene expression and decreases liver fibrosis. FIG. 3A shows the relative transcript levels determined by RT-qPCR. n=6, *$p<0.05$; **$p<0.01$; NS, not significant. MiR-27 targets Foxo1 and Ppara are significantly upregulated when the miR-27a is blocked in vivo, while expression of the fibrosis associated collagen 4a1 (Col4a1) is decreased. FIG. 3B provides an image of trichrome staining of liver sections from ASO27-treated Mdr2 mutant mice. A qualitative decrease in bridging fibrosis is observed. FIG. 3C provides the serum levels of total bile acid. FIG. 3D shows that liver hydroxyproline levels are lower in ASO27-treated Mdr2 mutant mice relative to ASOctrl treatment. Heterozygotes (het): n=4-8; mutants: n=6-10; *$p<0.05$; **$p<0.01$; NS, not significant.

Figure 4:
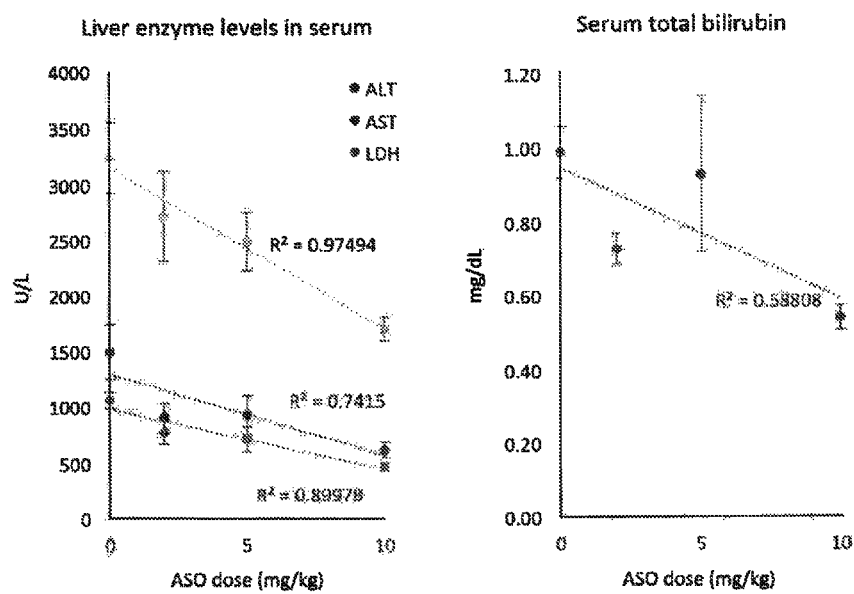

FIG. 4 provides graphs of the serum level of commonly used serum indicators of liver injury (left panel): lactate dehydrogenae (LDH), aspartate transaminase (AST); and alanine transaminase (ALT), and of cholestasis (total bilirubin, right panel) in Mdr2 mutant mice treated with 0, 2, 5, or 10 mg/kg ASO27.

DETAILED DESCRIPTION OF THE INVENTION

MicroRNAs are regulatory molecules that fine tune gene expression and are an emerging class of biomarkers in several diseases. However, the role of microRNAs in cholestasis was unknown. Herein, it has been discovered that several miRNAs are induced in diverse models of cholestasis and that two miRNAs in particular strongly contribute to pathogenesis. More specifically, the results provided herein demonstrate that the miR-23a/miR-27a/miR-24-1 (hereafter, miR-27a cluster) and miR-183/miR-96/miR-182 (hereafter, miR-182 cluster) clusters contribute to cholestatic injury and/or fibrosis. Further, the inhibition of either the miR-27a and/or miR-182 cluster ameliorates the cholestatic phenotype in a mouse model of progressive familial intrahepatic cholestasis (PFIC3), indicating that the induction of these miRNAs is pathogenic. More specifically, liver injury was decreased and less fibrosis was observed in mice treated with miR-27a and/or miR-182 antisense oligonucleotides.

It has been discovered herein that the microRNAs miA-27a and miR-182 are induced in models of hepatic cholestasis and in human biliary atresia liver samples. Biliary atresia (BA) is a fibro-inflammatory liver disease of infants in which a primary insult of unknown etiology leads to progressive T-cell mediated destruction of the extrahepatic biliary system (Bezerra, J. A. (2005) Pediatr. Transplant 9:646-651; Hartley et al. (2009) Lancet 374:1704-1713; Schreiber et al. (2002) J. Pediatr. Gastroenterol. Nutr., 35:S11-16; Mieli-Vergani et al. (2009) Semin. Immunopathol., 31:371-381). To test the function of these microRNAs in cholestasis, antisense oligonucleotides blocking miR-27a or miR-182 were injected into cholestatic mice. The cholestatic mice have mutations in the Mdr2 gene, resulting in a progressive cholestatic disease that duplicates the disease progressive familial intrahepatic cholestasis type 3 (PFIC-3) in humans. In comparison to control mice, the mice injected with antisense oligonucleotides directed to miR-27a or miR-182 (particularly miR-27a) had less evidence of liver injury (e.g., lower serum aspartate aminotransferase (AST) and alanine aminotransferase (ALT)), less fibrosis (histologically and at the level of collagen gene expression), and slightly elevated total cholesterol (still within the normal range). Gene expression profiling on these mice reveal widespread gene expression changes consistent with decreased stellate cell activation.

Gene ID: 407010 and GenBank Accession No. NR 029495 provide the nucleotide sequence of human miR-23a. More specifically, GenBank Accession No. NR_029495 provides the precursor sequence:

```
                                           (SEQ ID NO: 1)
1    ggccggctgg ggttcctggg gatgggattt gcttcctgtc 41   acaaatcaca ttgccaggga ttccaaccg acc,
``` wherein the strands (positions 9-30 and positions 45-65) of the miRNA duplex are underlined. The mature sequences of miR-23a are: ggggutccuggggaugggauuu (SEQ ID NO: 2) and aucacauugccagggauuucc (SEQ ID NO: 3).

Gene ID: 407018 and GenBank Accession No. NR_029501 provide the nucleotide sequence of human miR-27a. More specifically, GenBank Accession No. NR_029501 provides the precursor sequence:

```
                                           (SEQ ID NO: 4)
1    ctgaggagca gggcttagct gcttgtgagc agggtccaca 41   ccaagtcgtg ttcacagtgg ctaagttccg cccccag,
``` wherein the strands (positions 10-31 and positions 51-71) of the miRNA duplex are underlined. The mature sequences of miR-27a are: agggcuuagcugcuugugagca (SEQ ID NO: 5) and uucacaguggcuaaguuccgc (SEQ ID NO: 6).

Gene ID: 407012 and GenBank Accession No. NR_029496 provide the nucleotide sequence of human miR-24-1. More specifically, GenBank Accession No. NR_029496 provides the precursor sequence:

```
                                           (SEQ ID NO: 7)
1    ctccggtgcc tactgagctg atatcagttc tcattttaca 41   cactggctca gttcagcagg aacaggag,
``` wherein the strands (positions 7-28 and positions 44-65) of the miRNA duplex are underlined. The mature sequences of miR-24-1 are: ugccuacugagcugauaucagu (SEQ ID NO: 8) and uggcucaguucagcaggaacag (SEQ ID NO: 9).

Gene ID: 406959 and GenBank Accession No. NR_029615 provide the nucleotide sequence of human miR-183. More specifically, GenBank Accession No. NR_029615 provides the precursor sequence:

```
                                           (SEQ ID NO: 10)
1    ccgcagagtg tgactcctgt tctgtgtatg gcactggtag 41   aattcactgt gaacagtctc agtcagtgaa ttaccgaagg 81   gccataaaca gagcagagac agatccacga,
``` wherein the strands (positions 27-48 and positions 66-87) of the miRNA duplex are underlined. The mature sequences of miR-183 are: uauggcacugguagaauucacu (SEQ ID NO: 11) and gugaauuaccgaagggccauaa (SEQ ID NO: 12).

Gene ID: 407053 and GenBank Accession No. NR_029512 provide the nucleotide sequence of human miR-96. More specifically, GenBank Accession No. NR_029512 provides the precursor sequence:

```
                                           (SEQ ID NO: 13)
1    tggccgattt tggcactagc acatttttgc ttgtgtctct 41   ccgctctgag caatcatgtg cagtgccaat atgggaaa,
``` wherein the strands (positions 9-31 and positions 52-73) of the miRNA duplex are underlined. The mature sequences of miR-96 are: uuuggcacuagcacauuuuugcu (SEQ ID NO: 14) and aaucaugugcagugccaauaug (SEQ ID NO: 15).

Gene ID: 406958 and GenBank Accession No. NR_029614 provide the nucleotide sequence of human miR-182. More specifically, GenBank Accession No. NR 029614 provides the precursor sequence:

```
                                           (SEQ ID NO: 16)
1    gagctgcttg cctcccccg tttttggcaa tggtagaact 41   cacactggtg aggtaacagg atccggtggt tctagacttg 81   ccaactatgg ggcgaggact cagccggcac,
``` wherein the strands (positions 23-46 and positions 67-87) of the miRNA duplex are underlined. The mature sequence of miR-182 is: uuuggcaaugguagaacucacacu (SEQ ID NO: 17) and ugguucuagacuugccaacua (SEQ ID NO: 18).

In accordance with the instant invention, methods of inhibiting (e.g., reducing), preventing, and/or treating a liver injury/disorder/disease are provided. In a particular embodiment, the liver injury/disorder/disease is fibrotic (e.g., fibrotic liver disease). In a particular embodiment, the liver injury/disorder/disease is cholestasis and/or a cholestasis associated disease or disorder. In a particular embodiment, the method comprises administering at least one inhibitory nucleic acid molecule (e.g., an antisense oligonucleotide) which specifically hybridizes (e.g., at least 80%, at least 85%, at least 90%, at least 95% or more basepair identity (complementarity)) to or is completely complementary (i.e., 100% base pairing (though with different lengths permitted))

to the miR-27a and/or miR-182 cluster to a subject in need thereof. The antisense oligonucleotides may comprise a sequence which specifically hybridizes to or is completely complementary to the mature or precursor microRNA. In a particular embodiment, the antisense oligonucleotides comprise a sequence which specifically hybridizes to or is completely complementary to the major microRNA product and not the passenger strand (e.g., the antisense oligonucleotides may target 5'-uucacaguggcuaaguuccgc (SEQ ID NO: 6) for miR-27a or 5'-uuuggcaaugguagaacucacacu (SEQ ID NO: 17) for miR-182). In a particular embodiment, the antisense oligonucleotide specifically hybridizes to or is completely complementary to miR-27a and/or miR-182. In a particular embodiment, the method comprises the administration of at least one antisense oligonucleotide to each of miR-27a and miR-182 to a subject in need thereof.

The treatment of cholestatic liver injury by the methods of the instant invention has broad application against a variety of conditions, diseases, or disorders associated with cholestatic liver. Indeed, cholestatic liver is a symptom and/or indication of a variety of diseases and disorders. Diseases or disorders associated with cholestasis include, without limitation, biliary atresia, cystic fibrosis, primary sclerosing cholangitis, primary biliary cirrhosis, viral hepatitis, cholestasis hepatitis (cholangiolitic hepatitis), Alagille syndrome, PFIC 1-3, and the like. The methods of the instant invention may further comprise the administration of at least one other agent, therapeutic, or drug for the treatment of cholestasis and/or the disease or disorder associated with cholestasis. For example, ursodiol may be co-delivered for the treatment of primary biliary cirrhosis.

The antisense oligonucleotides of the instant invention may be administered directly or in a delivery vehicle. In a particular embodiment, the antisense oligonucleotides are delivered in an expression vector (e.g., a plasmid or viral vector). In other words, the antisense oligonucleotides of the instant invention may be encoded within an expression vector. An expression vector allows for the expression of the sequences encoded within the nucleic acid construct and/or for the intracellular delivery of the construct. The promoter of the expression vector may be particularly suited for the expression of (short) RNA molecules. Examples of such promoters include, but are not limited to, RNA polymerase II promoters, the T7 RNA polymerase promoter, and RNA polymerase III promoters (e.g., U6 and H1) (see, e.g., Myslinski et al. (2001) Nucl. Acids Res., 29:2502-09). In a particular embodiment, the expression vector is a viral vector. The viral vector may be RNA or DNA based. Examples of viral vectors include, without limitation, adenoviral, retroviral, lentiviral, adeno-associated virus, herpesviral, and vaccinia virus. In a particular embodiment, the viral vector capable of transducing the desired cell type (e.g., liver cells). In a particular embodiment, the viral vector is an adeno-associated viral vector (e.g., AAV 2/8). AAV vectors can be used to inhibit liver miRNAs in vivo (Kota et al. (2009) Cell 137:1005-17; Xie et al. (2012) Nat. Methods 9:403-9).

For example, the AAV 2/8 pseudo-typed recombinant viral vector may be used to deliver antisense oligonucleotides to the liver. Self-complementary AAV (scAAV) constructs may also be used to drive expression in vivo in hepatocytes with high efficiency (Kota et al. (2009) Cell 137:1005-17). The adeno-associated viral vector may be of a serotype selected from the group consisting of AAV1, AAV2, AAV3, AAV4, AAV5, AAV6, AAV7, AAV8, AAV9, AAV10, AAV11, AAV12, and hybrids thereof (e.g., a combinatorial hybrid of 2, 3, 4, 5, or more serotypes). The adeno-associated viral vector may be a hybrid AAV vectors having a capsid protein (e.g., any one of AAV serotypes 1-12) and genome (e.g., AAV serotype 2) from different AAV. In a particular embodiment, the adeno-associated viral vector is AAV2/8. Methods of synthesizing and preparing adeno-associated viral vectors are well known in the art. Other delivery vehicles include, without limitation lipid based vehicles (e.g., liposomes) and biodegradable polymer microspheres.

As stated hereinabove, the antisense oligonucleotides of the instant invention specifically hybridize with or are completely complementary to the target miRNA(s) (mature or precursor form). The antisense oligonucleotide may be RNA or DNA. The antisense oligonucleotide may be single-stranded or double-stranded, particularly single-stranded (although the single-stranded oligonucleotide may form double-stranded structures such as hairpins). The antisense oligonucleotide will typically be from about 10 to about 100 nucleotides in length, more typically from about 10 to about 50 nucleotides, about 10 to about 30 nucleotides or about 15 to about 25 nucleotides. In a particular embodiment, the antisense oligonucleotide is at least 15 nucleotides in length. The antisense oligonucleotide may have at least 80%, at least 85%, at least 90%, at least 95%, at least 97%, or 100% complementarity to the target miRNA(s), particularly the sequences set forth hereinabove (e.g., any one of SEQ ID NOs: 1-18). The antisense oligonucleotide may have at least 80%, at least 85%, at least 90%, at least 95%, at least 97%, or 100% identity with a sequence that is the complement to the target miRNA(s), particularly the sequences set forth hereinabove (e.g., any one of SEQ ID NOs: 1-18). The antisense oligonucleotides may comprise additional nucleotides 5' or 3' to the sequence which has complementarity with the target miRNA. For example, the antisense oligonucleotide may comprise at least 1, 2, 3, 4, 5, or up to 10 or 20 nucleotides 5' or 3' to region having complementarity to the target. The additional nucleotides may have complementarity to each other (e.g., regions of homology) to create hairpin structures.

The antisense oligonucleotide may comprise at least one nucleotide analog. The nucleotide analogs may be used, for example, to increase annealing affinity, specificity, bioavailability in the cell and organism, cellular and/or nuclear transport, stability, and/or resistance to degradation. Nucleotide analogs include, without limitation, nucleotides with phosphate modifications (e.g., those comprising one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions (see, e.g., Hunziker and Leumann (1995) Nucleic Acid Analogues: Synthesis and Properties, in Modern Synthetic Methods, VCH, 331-417; Mesmaeker et al. (1994) Novel Backbone Replacements for Oligonucleotides, in Carbohydrate Modifications in Antisense Research, ACS, 24-39)); nucleotides with modified sugars or sugar modifications such as 2'-O-methyl (2'-O-methylnucleotides), 2'-fluoro, 2'-alpha-flouro, and 2'-O-methyloxyethoxy; and nucleotide mimetics such as, without limitation, peptide nucleic acids (PNA), morpholino nucleic acids, cyclohexenyl nucleic acids, anhydrohexitol nucleic acids, glycol nucleic acid, threose nucleic acid, and locked nucleic acids (LNA). Nucleotide analogs are described in U.S. Patent Application Publication No. 2005/0118605 and U.S. Pat. Nos. 5,886,165; 6,140,482; 5,693,773; 5,856,462; 5,973,136; 5,929,226; 6,194,598; 6,172,209; 6,175,004;

6,166,197; 6,166,188; 6,160,152; 6,160,109; 6,153,737; 6,147,200; 6,146,829; 6,127,533; and 6,124,445. In a particular embodiment, the antisense oligonucleotide comprises at least one modification selected from the group consisting of 2'-O-methoxyethyl, 2'-flouro, 2'-alpha-flouro, and phosphorothioate backbone.

In a particular embodiment, the antisense oligonucleotide is an antagomir, tough decoy (TuD), or sponge. An antagomir comprises a single miRNA target (i.e., it is complementary to the miRNA). An miRNA sponge comprises two or more miRNA target sequences arranged tandemly (described in Ebert et al., RNA (2010) 16: 2043-2050; incorporated by reference herein). The miRNA sponge may comprise a bulge in the center of the miRNA target sequences (i.e., may be a bulged sponge). TuDs are bulged hairpin RNAs complementary in sequence to the mature miRNA of interest, with a mispaired region (e.g., a 4 or more nucleotide region (e.g., about 4 to about 50 nucleotides, particularly about 4 to about 10, 15, or 20 nucleotides) in the center to prevent cleavage of the TuD transcript (Ebert et al. (2010) Current Biol., 20:R858-61; Haraguchi et al. (2009) Nuc. Acids Res., 37:e43; Bak et al. (2013) RNA 19:280-293; incorporated by reference herein). The TuD comprises regions of homology (e.g., at least about 5 nucleotides) surrounding two miRNA target sequences, thereby generating an internal bulge exposing the two miRNA target sequences in the mature form. The TuDs may also be arranged and expressed in a tandem arrangement.

In accordance with the instant invention, methods of detecting the presence of liver injury (e.g., cholestasis) or increased risk of developing liver injury (e.g., cholestasis) are provided. In a particular embodiment, the method comprises detecting the presence and/or expression of the miR-27a and/or miR-182 cluster, particularly miR-27a and/or miR-182, in a biological sample obtained from a subject. An increase in the amount of miR-27a and/or miR-182 compared to a healthy sample (e.g., a biological sample from a patient without cholestasis) is indicative of the presence of cholestasis or an increased risk for developing cholestasis. In a particular embodiment, the method further comprises obtaining the biological sample from the subject. In a particular embodiment, the detection of the microRNAs allows for the classification, diagnosis and/or prognosis of the cholestasis (e.g., the greater the increase in expression correlates with an increased severity of or risk for cholestasis). The method of the instant invention may comprise the detection of the mature and/or precursor forms of the microRNA.

Any method for detecting the microRNAs may be used in the instant invention. For example, in situ and/or in vitro methods may be used. Examples of detection methods that may be used include, without limitation, contacting the nucleic acid molecules (optionally isolated) of a biological sample with a probe, in situ hybridization, microarray (e.g., a microarray of probes) analysis, affinity matrices, Northern blot analysis, and PCR (e.g., RT-PCR, real-time quantitative RT-PCR, etc.). Inasmuch as RNA is sensitive to degradation, the nucleic acids of the biological sample may be converted to DNA (e.g., through reverse transcription) prior to analysis. In a particular embodiment, the detection method comprises the use of at least one probe or primer which specifically hybridizes (e.g., at least 80%, at least 85%, at least 90%, at least 95% or more basepair identity) to or is completely complementary (i.e., 100% base pairing (though with different lengths permitted)) to the mature or precursor microRNA.

The present invention also encompasses compositions comprising 1) at least one antisense oligonucleotide as described herein and 2) at least one pharmaceutically acceptable carrier. The antisense oligonucleotide may be encoded within an expression vector. In a particular embodiment, the composition comprises at least one antisense oligonucleotides to each of miR-27a and miR-182. Such compositions may be administered, in a therapeutically effective amount, to a patient in need thereof for the treatment of cholestasis. The compositions may further comprise at least one other agent for the treatment of cholestasis and/or a disease or disorder associated with cholestasis. Alternatively, the other agents for treating cholestasis or associated disease or disorder may be contained within a separate composition with at least one pharmaceutically acceptable carrier for sequential and/or simultaneous administration. Composition(s) of the instant invention may be contained within a kit.

The compositions of the present invention can be administered by any suitable route, for example, by injection (e.g., for local (direct, including to or within the kidneys) or systemic administration), orally, pulmonary, topical, nasally or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered intravenously or directly to the liver. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween® 80, polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington: The Science and Practice of Pharmacy, Philadelphia, Pa. Lippincott Williams & Wilkins). The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

The dose and dosage regimen of the molecule of the invention that is suitable for administration to a particular patient may be determined by a physician considering the patient's age, sex, weight, general medical condition, and the specific condition and severity thereof for which the inhibitor is being administered. The physician may also consider the route of administration, the pharmaceutical carrier, and the molecule's biological activity.

Selection of a suitable pharmaceutical preparation depends upon the method of administration chosen. For example, the molecules of the invention may be administered by direct injection into renal tissue or into the area surrounding the kidneys. In this instance, a pharmaceutical preparation comprises the molecules dispersed in a medium that is compatible with the renal tissue.

Molecules of the instant invention may also be administered parenterally by intravenous injection into the blood stream, or by subcutaneous, intramuscular, intrathecal, or intraperitoneal injection. Pharmaceutical preparations for parenteral injection are known in the art. If parenteral injection is selected as a method for administering the molecules, steps should be taken to ensure that sufficient amounts of the molecules reach their target cells to exert a biological effect. The lipophilicity of the molecules, or the pharmaceutical preparation in which they are delivered, may have to be increased so that the molecules can arrive at their target locations. Methods for increasing the lipophilicity of a molecule are known in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, topical, or parenteral. In preparing the molecule in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to animals with cholestasis, and the minimal and maximal dosages may be determined based on the results of significant reduction of the cholestasis and side effects as a result of the treatment. Appropriate dosage unit may also be determined by assessing the efficacy of the treatment in combination with other standard therapies. The dosage units of the molecules may be determined individually or in combination with each therapy according to greater reduction of symptoms and disease.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention:

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., cholestasis) resulting in a decrease in the probability that the subject will develop the condition.

As used herein, a "biological sample" refers to a sample of biological material obtained from a subject, preferably a human subject, including a tissue, a tissue sample, a cell sample, a tumor sample, and a biological fluid (e.g., blood, urine, or amniotic fluid).

As used herein, "diagnose" refers to detecting and identifying a disease or disorder in a subject. The term may also encompass assessing or evaluating the disease or disorder status (progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality, the likelihood of getting or risk of cholestasis). In other words, the term "prognosis" refers to providing a prediction of the probable course and outcome of a disease/disorder or the likelihood of recovery from the disease/disorder.

A "therapeutically effective amount" of a compound or a pharmaceutical composition refers to an amount effective to prevent, inhibit, or treat a particular disorder or disease and/or the symptoms thereof.

As used herein, the term "subject" refers to an animal, particularly a mammal, particularly a human.

As used herein, the term "cholestasis" refers to any condition in which the flow of bile from the liver to the duodenum is blocked or reduced/inhibited. Cholestasis may be intrahepatic (i.e., occurring inside the liver) or extrahepatic (i.e., occurring outside the liver). Bile flow failures may arise anywhere in the hepatic and biliary system.

As used herein, the terms "microRNA," "miR," and "miRNA" may refer to unprocessed (e.g., precursor) or processed (e.g., mature) microRNAs, unless otherwise indicated. MicroRNAs (miRNAs) are a class of short endogenous RNAs that typically act as post-transcriptional regulators of gene expression by base-pairing with their target mRNAs. Generally, mature miRNAs are processed sequentially from longer hairpin transcripts (precursor miRNA) by RNAse III ribonucleases (Lee et al. (2003) Nature 425:415-419; Hutvagner et al. (2001) Science 293:834-838; Ketting et al. (2001) Genes Dev., 15:2654-2659). The unprocessed or precursor microRNA typically comprises an RNA oligonucleotide of about 70 to about 100 nucleotides in length. MicroRNA precursors may be processed by digestion with an RNAse (e.g., Dicer, RNAse III, etc.) into an active (mature) microRNA. Mature microRNAs are typically RNA oligonucleotides of about 17 to about 25 nucleotides. The mature microRNA can be obtained from the precursor through natural processing routes (e.g., using intact cells or cell lysates) or by synthetic processing routes (e.g., using isolated processing enzymes). The mature microRNAs may also be produced directly by biological or chemical synthesis (i.e., without having to be processed from the precursor). The microRNA may be single or double stranded, but are typically single-stranded.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10-500, about 10-250, about 10-100, about 10-50, about 15-30, about 15-25, or about 10-20 nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. A probe may be tagged or labeled (i.e., attached to an entity making it possible to identify a compound to which it is associated (e.g., fluorescent or radioactive tag)).

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 10-25 or more nucleotides in length, but can be significantly longer. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12 20° C. below the Tm of the hybrid. In regards to the nucleic acids of the current invention, a moderate stringency hybridization is defined as hybridization in 6× SSC, 5×Denhardt's solution, 0.5% SDS and 100 µg/ml denatured salmon sperm DNA at 42° C., and washed in 2× SSC and 0.5% SDS at 55° C. for 15 minutes. A high stringency hybridization is defined as hybridization in 6× SSC, 5×Denhardt's solution, 0.5% SDS and 100 µg/ml denatured salmon sperm DNA at 42° C., and washed in 1× SSC and 0.5% SDS at 65° C. for 15 minutes. A very high stringency hybridization is defined as hybridization in 6× SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "promoters" or "promoter" as used herein can refer to a DNA sequence that is located adjacent to a DNA sequence that encodes a recombinant product (nucleic acid molecule or protein). A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and/or translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The following example provides illustrative methods of practicing the instant invention and is not intended to limit the scope of the invention in any way.

EXAMPLE

To test the hypothesis that cholestasis induces changes in hepatic miRNA levels, large-scale profiling of liver miRNA was performed in two mouse models of cholestasis:

1) Bile duct ligation (BDL) model: a surgical model in which cholestasis is induced by physical obstruction (via ligature) of the common bile duct.

2) The Mdr2$^{-/-}$ genetic mouse model: this model is directly analogous to the pediatric liver disorder progressive familial intrahepatic cholestasis (PFIC3). Mdr2 (MDR3 in humans) encodes a phospholipid flippase that traffics protective phospholipids into bile canaliculi. In Mdr2 deficiency, lower phospholipid levels in bile lead to obstructive cholestasis and a progressive cholangiopathy (Jacquemin, E. (2001) Seminars Liver Dis., 21:551-62).

FIG. 1 shows that the miR-182 and miR-27a miRNA clusters are significantly up-regulated in both BDL and Mdr2$^{-/-}$ mouse liver. Significantly, miRNAs from both clusters are also elevated in human cholestatic clinical samples (children with biliary atresia) relative to age-matched non-cholestatic controls (FIG. 1). The degree of elevation is similar in both mouse and human: ~2.5-fold increase in the miR-27a cluster members, and ~10-fold in miR-182. Notably, the miR-27a cluster miRNAs are more abundant in liver than those of the miR-182 cluster. Further, miR-27a—but not miR-27b—was determined to be significantly more abundant in Mdr2$^{-/-}$ mice compared to wild-type mice.

Experiments also indicate that the induction of these miRNAs in cholestatic liver is due to elevated bile acids. Indeed, the expression of both clusters is induced in HepG2 cells exposed to either cholic or chenodeoxycholic acid.

MiRNAs are negative regulators of gene expression, and each may decrease the expression of hundreds of genes. The miRNA induction observed herein may be part of a physiological adaptive response to cholestasis. Alternatively, elevation of these miRNAs may be maladaptive and may contribute to disease progression. To distinguish between these alternatives, miR-27a and miR182 were inhibited individually in male Mdr2$^{-/-}$ mice. The mice were injected intraperitoneally with 20 mg/kg of control antisense oligonucleotide (ASOctrl), antisense oligonucleotide to miR-27a (ASO27), or antisense oligonucleotide miR182 (ASO182) at 8, 9, 10, and 11 weeks of age. Liver tissue, liver RNA, and serum were collected at week 12. Serum biochemistry revealed a decrease in both aspartate aminotransferase (AST) and alanine aminotransferase (ALT) levels when either miR-27a or miR-182 were inhibited in vivo, as were the liver mass and liver to body weight ratio (FIG. 2). Hepatic nodularity and fibrosis were reduced (FIG. 3), and this is supported by 2-fold reductions in Col4a1 gene expression and liver hydroxyproline in ASO27 relative to controls. Treatment with ASO182 had an intermediate effect. Significant differences between groups in the total bile acid concentration in serum were not detected, but there may be significant differences in the composition of the circulating bile acid pool, which may contribute to differences in the degree of fibrosis (e.g., due to a shift in the hydrophobicity).

To further demonstrate the effectiveness of this therapy, Mdr2 mutant males were injected intraperitoneally with PBS (0) or PBS containing 2, 5, or 10 mg/kg of ASO27 (n=8 per treatment) at 8, 9, 10, and 11 weeks of age. At 12 weeks of age the mice were euthanized following IACUC protocol, and liver tissue, liver RNA, and serum were collected. Commonly used serum indicators of liver injury (lactate dehydrogenae (LDH); aspartate transaminase (AST); and alanine transaminase (ALT)) and of cholestasis (total bilirubin) showed a linear, dose-dependent decrease with increasing dose of ASO27. These results indicate that both liver injury and cholestasis are ameliorated by inhibition of the miR-27a cluster.

These results indicate that miRNA manipulation represents a new avenue for therapeutic intervention in cholestatic liver disease.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating and/or inhibiting cholestasis in a subject, said method comprising administering to said subject at least one antisense oligonucleotide, wherein said antisense oligonucleotide specifically hybridizes with miR-27a.

2. The method of claim 1, wherein said method further comprises administering at least one antisense oligonucleotide which specifically hybridizes with miR-182.

3. The method of claim 1, wherein said antisense oligonucleotide comprises a sequence which is at least 90% complementary to SEQ ID NO: 6.

4. The method of claim 1, wherein said antisense oligonucleotide comprises at least one nucleotide analog.

5. The method of claim 1, wherein said antisense oligonucleotides are encoded in an expression vector.

6. The method of claim 1, wherein said antisense oligonucleotide is an antagomir, tough decoy, or sponge.

7. The method of claim 1, wherein said subject has liver fibrosis.

8. The method of claim 1, wherein said antisense oligonucleotide comprises a sequence which is completely complementary to SEQ ID NO: 6.

9. The method of claim 1, wherein said antisense oligonucleotide is 15 to 25 nucleotides in length.

10. The method of claim 4, wherein said nucleotide analog is a nucleotide with a sugar modification.

11. A method of treating and/or inhibiting cholestasis in a subject, said method comprising administering to said subject an antisense oligonucleotide, wherein said antisense oligonucleotide specifically hybridizes with miR-182.

12. The method of claim 11, wherein said method further comprises administering at least one antisense oligonucleotide which specifically hybridizes with miR-27a.

13. The method of claim 11, wherein said antisense oligonucleotide comprises a sequence which is at least 90% complementary to SEQ ID NO: 17.

14. The method of claim 11, wherein said antisense oligonucleotide comprises a sequence which is completely complementary to SEQ ID NO: 17.

15. The method of claim 11, wherein said antisense oligonucleotide is 15 to 25 nucleotides in length.

16. The method of claim 11, wherein said antisense oligonucleotide comprises at least one nucleotide analog.

17. The method of claim 16, wherein said nucleotide analog is a nucleotide with a sugar modification.

18. The method of claim 11, wherein said antisense oligonucleotides are encoded in an expression vector.

19. The method of claim 11, wherein said antisense oligonucleotide is an antagomir, tough decoy, or sponge.

20. The method of claim 11, wherein said subject has liver fibrosis.

\* \* \* \* \*

UNITED STATES PATENT AND TRADEMARK OFFICE
CERTIFICATE OF CORRECTION

PATENT NO. : 9,932,583 B2
APPLICATION NO. : 15/119036
DATED : April 3, 2018
INVENTOR(S) : Joshua R. Friedman and Nicholas J. Hand Page 1 of 1

It is certified that error appears in the above-identified patent and that said Letters Patent is hereby corrected as shown below:

In the Specification

At Column 1, Lines 9-11:
Please delete:
"Grant No. R01 DK079881 awarded by the National Institute of Diabetes and Digestive and Kidney Diseases (NIDDK). The Government has certain rights in this invention."

And insert therefor:
--grant number DK079881 awarded by the National Institutes of Health. The government has certain rights in the invention.--

Signed and Sealed this
Seventeenth Day of March, 2020

Andrei Iancu
*Director of the United States Patent and Trademark Office*